(12) United States Patent
Hur

(10) Patent No.: US 7,909,039 B2
(45) Date of Patent: Mar. 22, 2011

(54) OPERATING STAPLE AND INTRALUMINAL STAPLER FOR OPERATION HAVING THE OPERATING STAPLE

(75) Inventor: Yoon-Seok Hur, Seoul (KR)

(73) Assignee: Inha-Industry Partnership Institute, Yonghyeon-Dong, Nam-Gu, Incheon (KR)

( * ) Notice: Subject to any disclaimer, the term of this patent is extended or adjusted under 35 U.S.C. 154(b) by 0 days.

(21) Appl. No.: 11/574,304

(22) PCT Filed: Nov. 24, 2004

(86) PCT No.: PCT/KR2004/003051
§ 371 (c)(1),
(2), (4) Date: Feb. 26, 2007

(87) PCT Pub. No.: WO2006/028314
PCT Pub. Date: Mar. 16, 2006

(65) Prior Publication Data
US 2007/0233126 A1 Oct. 4, 2007

(30) Foreign Application Priority Data

Sep. 10, 2004 (KR) ........................ 10-2004-0072540

(51) Int. Cl.
*A61B 19/10* (2006.01)
*A61B 17/068* (2006.01)
(52) U.S. Cl. ....... 128/898; 227/19; 227/152; 227/176.1; 606/219
(58) Field of Classification Search ............... 227/176.1, 227/19, 152; 606/219; 128/898
See application file for complete search history.

(56) References Cited

U.S. PATENT DOCUMENTS

| | | | | |
|---|---|---|---|---|
| 3,079,606 | A | * | 3/1963 | Bobrov et al. ................... 227/76 |
| 3,490,675 | A | * | 1/1970 | Green et al. ..................... 227/19 |
| 4,304,236 | A | * | 12/1981 | Conta et al. ................. 227/179.1 |
| 4,607,638 | A | * | 8/1986 | Crainich ........................ 606/219 |
| 4,633,874 | A | * | 1/1987 | Chow et al. ................. 227/176.1 |
| 4,767,044 | A | * | 8/1988 | Green ............................. 227/19 |
| 5,104,025 | A | | 4/1992 | Main |
| 5,111,987 | A | * | 5/1992 | Moeinzadeh et al. ..... 227/180.1 |
| 5,222,975 | A | | 6/1993 | Crainich |
| 5,258,009 | A | * | 11/1993 | Conners ........................ 606/219 |
| 5,342,396 | A | * | 8/1994 | Cook ............................ 606/219 |
| 5,489,058 | A | * | 2/1996 | Plyley et al. ................ 227/176.1 |

(Continued)

FOREIGN PATENT DOCUMENTS

WO WO 94/20030 9/1994

(Continued)

*Primary Examiner* — Rinaldi I Rada
*Assistant Examiner* — Gloria R Weeks
(74) *Attorney, Agent, or Firm* — Lexyoume IP Group, PLLC.

(57) ABSTRACT

An operating staple is provided in which stability during an operation is enhanced by firmly suturing an operating portion and an intraluminal stapeler for operation having the operating staple. The operating staple closely sutures a first suturing tissue and a second suturing tissue contacting the first suturing tissue, and the operating staple includes: a center portion extending in close contact with a surface of the first suturingtissue; a pair of penetrating portions which is bent from both ends of the center portion and penetrates the first suturing tissue and the second suturing tissue; and a pair of leg portions which is bent from the respective penetrating portions, extends linearly, and closely bonds the first suturing tissue and the second suturing tissue to each other. Therefore, by utilizing the operating staple, the suturing tissues can be firmly sutured, thereby enhancing the stability during an operation.

2 Claims, 7 Drawing Sheets

U.S. PATENT DOCUMENTS

| | | | |
|---|---|---|---|
| 5,551,622 A | | 9/1996 | Yoon |
| 5,645,567 A | * | 7/1997 | Crainich ................. 606/219 |
| 5,667,527 A | * | 9/1997 | Cook ..................... 606/219 |
| 5,738,474 A | * | 4/1998 | Blewett ................. 411/473 |
| 6,488,196 B1 | * | 12/2002 | Fenton, Jr. ............. 227/175.1 |
| 7,287,682 B1 | * | 10/2007 | Ezzat et al. ............ 227/175.1 |
| 7,398,907 B2 | * | 7/2008 | Racenet et al. ......... 227/176.1 |
| 7,517,356 B2 | * | 4/2009 | Heinrich ................. 606/219 |
| 7,559,937 B2 | * | 7/2009 | de la Torre et al. ..... 606/142 |
| 7,635,073 B2 | * | 12/2009 | Heinrich ................ 227/175.1 |
| 7,641,095 B2 | * | 1/2010 | Viola ..................... 227/176.1 |

FOREIGN PATENT DOCUMENTS

WO      WO 97/12729      4/1997

* cited by examiner

[Fig. 5]
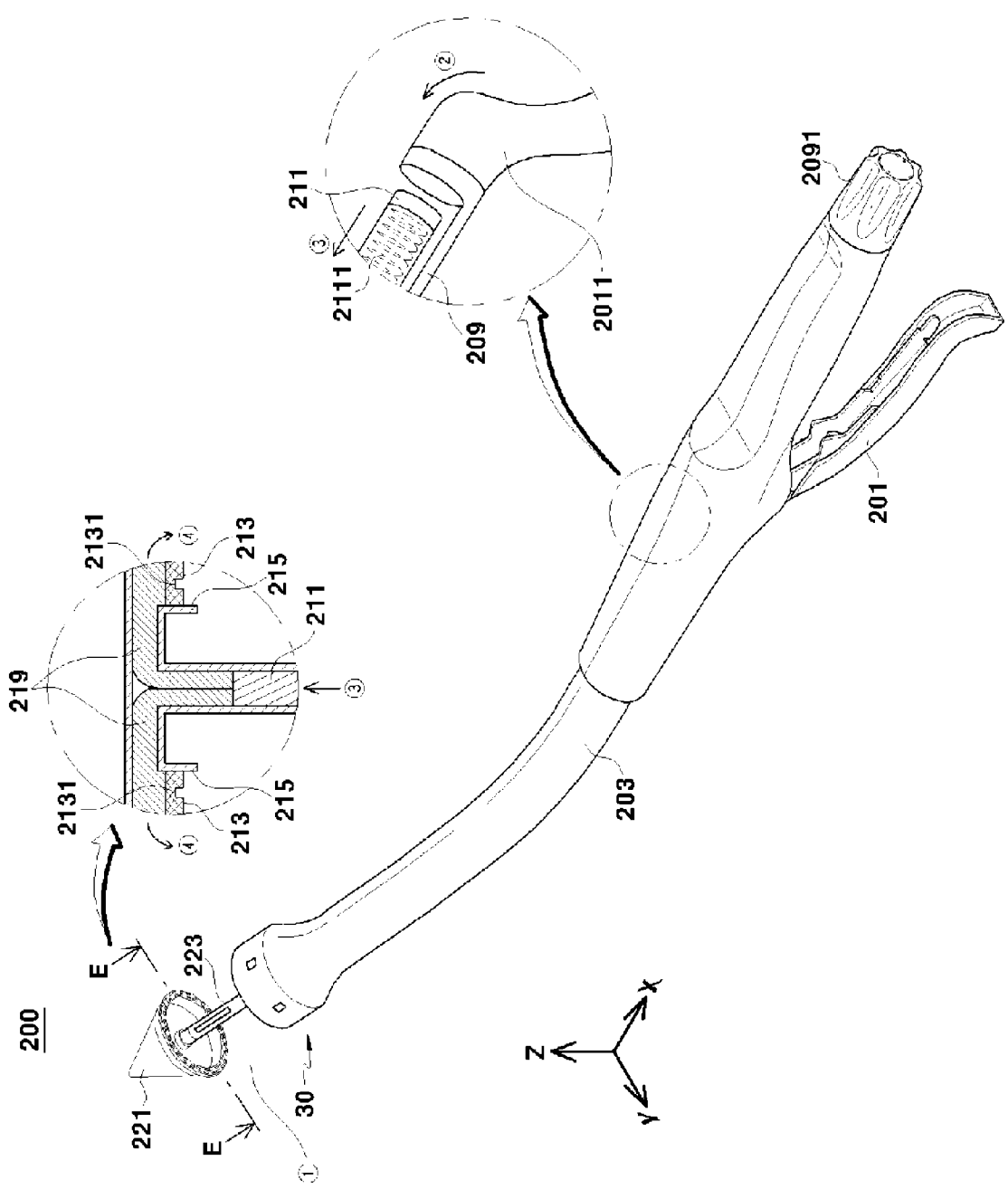

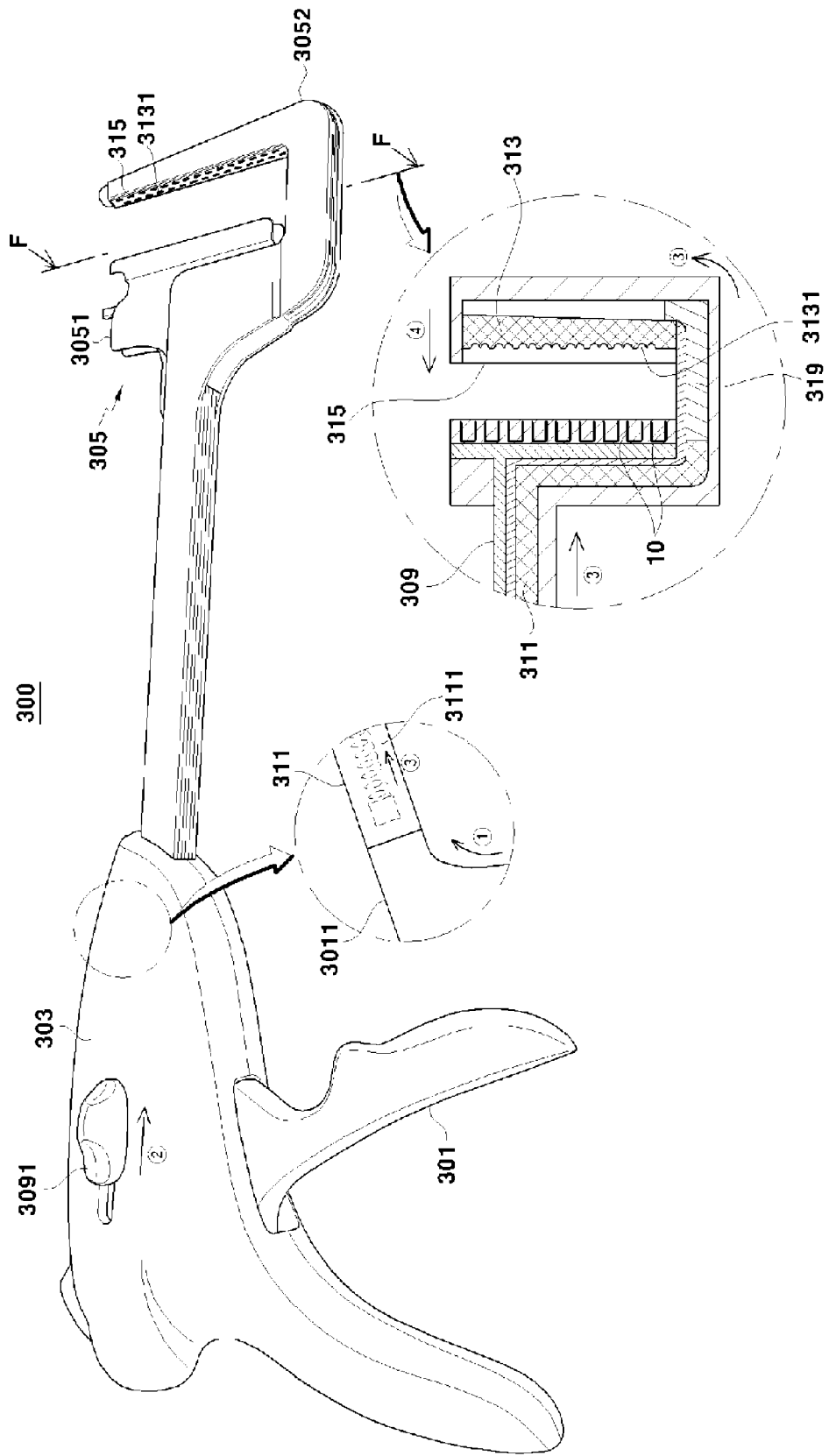
[Fig. 6]

[Fig. 7]
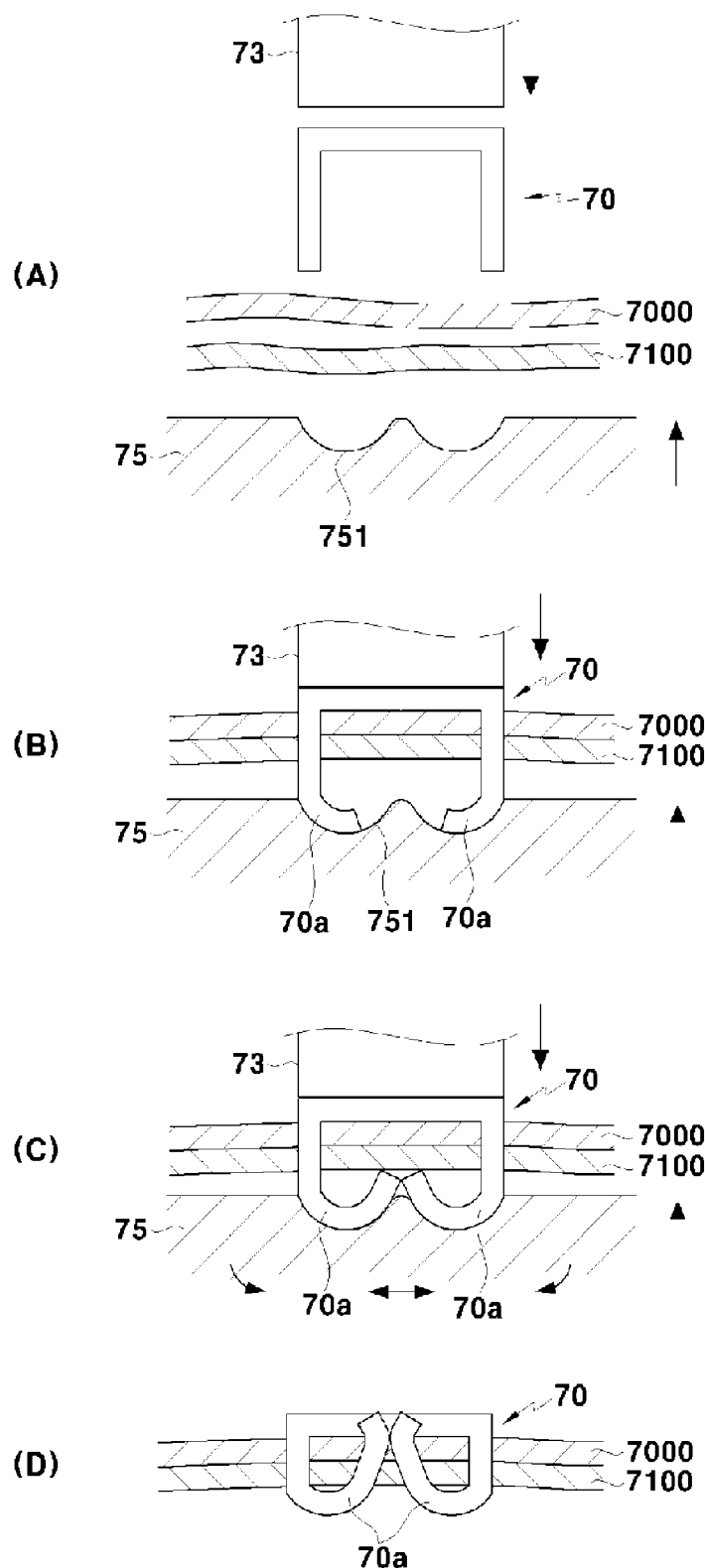
PRIOR ART

OPERATING STAPLE AND INTRALUMINAL STAPLER FOR OPERATION HAVING THE OPERATING STAPLE

TECHNICAL FIELD

The present invention relates to an operating staple and an intraluminal stapler for operation having the operating staple, and more particularly, to a staple in which stability during an operation is enhanced by firmly suturing an operating portion and an intraluminal stapler for operation having the staple.

BACKGROUND ART

In operations such as esophagus reconstruction after esophagus extraction, gastrectomy, small-intestine and large-intestine resections, etc., there have been steadily studied operating methods and instruments for more completely suturing both resected portions.

Specifically, among operations on the inside of a human body, for example, an operation of connecting an end of the esophagus, which is located at a position where it is difficult to perform a specific operation, to the small intestine at the inside of a diaphragm after a total gastrectomy, an operation of connecting the remaining portion of a rectum to a large intestine after resecting the rectum up to a portion close to an anus, etc. have many difficulties. That is, in order to anastomose the esophagus to the small intestine after performing the total gastrectomy, a major operation of cutting ribs and the diaphragm to enter a chest should have been performed. In a case of operation on the rectum, the anus should be removed and the large intestine should be exposed to the abdomen, so that a disorder of drawing out excrements should be left.

An intraluminal stapler was developed to overcome the difficulties of operation, which is used for anastomosing an esophagus to a small intestine or anastomosing intestines to each other, cutting off a specific portion, and anastomosing blood vessels to each other. Details of such an intraluminal stapler are disclosed in U.S. Pat. No. 5,104,025.

After cutting off an intestine, the cut-off ends of the intestine are sutured with the intraluminal stapler so as to keep the connection between the intestines. This process requires most time and labor in operations and also requires a constant result. The intraluminal stapler for simply and securely performing the process is classified into a circular stapler (EEA) and a linear stapler. The linear stapler is further classified into a stapler (GIA) cutting and suturing a tissue and a stapler (TA) only suturing a tissue.

In such intraluminal staplers, staples are pressed by a push member, penetrate an operating portion, and then are pressed by a support member having grooves, so that the staples are bent in an arc shape. The staples used in an operation on a human body have the same appearance as general stationery staples, but have a size and a material different from the stationery staples. Therefore, such a type has a bad influence on the sutured operating portions. Now, problems related to this shape will be described in more detail with reference to FIG. 7.

FIG. 7 is a schematic diagram illustrating working steps of the conventional staple, where the process of suturing a tissue using the staple is illustrated step by step. The state of suturing a tissue using the staple will be described as follows.

First, as shown in (A) of FIG. 7, at the upside, a staple 70 is pressed by a push member 73 and at the downside, a support member 75 having grooves 751 for bending the staple 70 is provided. The staple 70 penetrates suturing tissues 7000 and 7100 by pressing the staple 70 with the push member 73 in the upper arrow direction, and the support member 75 gets close to the lower portion of the suturing tissues 7000 and 7100 in the lower arrow direction.

Since the push member 73 and the support member 75 work simultaneously in this way, as shown in (A) of FIG. 7, leg portions 70a of the staple 70 extending downwardly come in contact with the grooves 751 of the support member 75 and the leg portions 70a are bent in a rounded shape while the staple 70 penetrates the suturing tissues 7000 and 7100.

As the push member 73 and the support member 75 are continuously moved in the arrow directions, as shown in (C) of FIG. 7, the leg portions 70a of the staple 70 are completely bent, come in contact with the lower portion of the suturing tissue 7100, and then closely suture the suturing tissues 7000 and 7100. However, since the leg portions 70a of the staple 70 are opposed to each other and bent in a rounded shape, as indicated by the central arrow, a repulsive force is applied to respective ends of the leg portions 70a. On the contrary, as indicated by both side arrows, an attractive force due to the bending is applied to the leg portions 70a close to the penetrated portions.

Accordingly, since tensions having different directions are applied to the same leg portions 70a, the tensions have an influence on the suturing tissues 7000 and 7100, so that the tensions are made uneven. Since the tensions are uneven, the suturing tissues positioned at the ends of the leg portions 70a may be bitten and torn, and the suturing tissues positioned at the leg portions 70a close to the penetrated portions may be lack of tension, thereby causing bleeding or leakage.

Specifically, when an excessive force is applied at the time of suturing the operating portion using the intraluminal stapler as shown in (D) of FIG. 7, the ends of leg portions 70a of the staple 70 may re-penetrate the suturing tissues 7000 and 7100 toward the upper portion of the suturing tissues 7000 and 7100. Therefore, total four holes are formed in the suturing tissues 7000 and 7100, thereby causing the bleeding from the suturing tissues 7000 and 7100. In addition, the sutured portion may be opened even after the operation, thereby requiring a re-operation.

DISCLOSURE OF INVENTION

Technical Problem

The present invention is contrived to solve the above problems, and it is an object of the present invention to provide a staple capable of firmly suturing tissues at the time of operating causing no bleeding and having a safe structure.

It is also an object of the present invention to provide an intraluminal stapler having the above staple and having an easy manipulation and a simple structure.

TECHNICAL SOLUTION

In order to accomplish the above objects, according to an aspect of the present invention, there is provided an operating staple for closely suturing a first suturing tissue and a second suturing tissue contacting the first suturing tissue, the operating staple comprising: a center portion extending in close contact with a surface of the first suturing tissue; a pair of penetrating portions which is bent from both ends of the center portion and penetrates the first suturing tissue and the second suturing tissue; and a pair of leg portions which is bent from the respective penetrating portions, extends linearly, and closely bonds the first suturing tissue and the second suturing tissue to each other.

The respective leg portions extending from the penetrating portions may be bent to form an acute angle together with the respective penetrating portions.

Here, the pair of leg portions may be bent to oppose each other.

Both ends of the pair of leg portions may be in contact with each other.

The operating staple may be made of a titanium plate.

The operating staple may be plurally attached in a parallel-line shape to the first suturing tissue and the second suturing tissue, thereby closely suturing the first suturing tissue and the second suturing tissue.

In addition, the operating staple may be plurally attached in a substantially circular shape to the first suturing tissue and the second suturing tissue, thereby closely suturing the first suturing tissue and the second suturing tissue.

According to another aspect of the present invention, there is provided an intraluminal stapler for operation having an operating staple, the intraluminal stapler comprising: a trigger provided at one side of the intraluminal stapler; an elastic member which comes in contact with an working portion of the trigger during manipulation of the trigger and extends through the inside of the intraluminal stapler; a support member which is connected to the elastic member and has a groove formed in the lower portion thereof, the groove bending both ends of the operating staple together with the elastic member; and a housing which has an inner space for receiving the support member and the ends of the operating staple having penetrated a suturing tissue, and which guides the support member to the ends of the operating staple in response to working of the elastic member.

The intraluminal stapler for operation according to the present invention may further comprise a push member which pushes the operating staple, such that the operating staple penetrates the suturing tissue, until the trigger comes in contact with the elastic member.

The intraluminal stapler for operation according to the present invention may further comprise a cutter which is spaced in parallel from a plurality of staples and cuts the suturing tissue in response to working of the push member.

The intraluminal stapler for operation according to the present invention may further comprise a sliding member which is located on the rear surface of the support member and pushes the support member in response to working of the elastic member.

ADVANTAGEOUS EFFECTS

As described above, by firmly and closely suturing the suturing tissues with the staples according to the present invention using the intraluminal staplers having various structures, it is easy to secure stability of an operation, and there is almost no bleeding from the sutured portion, thereby not causing sequelae after an operation.

In the operating staples according to the present invention, since the leg portions extend linearly and bring the suturing tissues in close contact with each other, the tensions around the sutured portion can be made uniform, thereby not causing the bleeding after an operation.

Since the leg portions of the staples are bent to form an acute angle about the penetrating portion, it is possible to firmly and closely suture the suturing tissues.

Further, since a pair of leg portions is bent to oppose each other, it is possible to more firmly and closely suture the suturing portions.

Since both ends of the pair of leg portions are in contact with each other, the staples can be firmly fixed to the suturing tissues.

Since the operating staples can be made of a titanium plate, the operating staples are not harmful to a human body and are excellent in durability, deformation, and maintenance after deformation.

Since the operating staples are attached in parallel or in a substantially circular shape to the suturing tissues to more firmly and closely suture the suturing tissues, sequelae after an operation can be reduced.

Since the intraluminal stapler for operation according to the present invention includes the housing having the inner space which receives the support member and in which the ends of the staples penetrating the suturing tissues are positioned, and guiding the support member toward the ends of the staples in response to the working of the elastic member, the suturing operation on the suturing tissues can be performed step by step, so that it is possible to firmly suture the suturing tissues.

Since the intraluminal stapler for operation according to the present invention further includes the push member pushing the staples such that the staples penetrate the suturing tissues until the trigger comes in contact with the elastic member, the step-by-step suturing operation described above can be securely embodied.

Since the intraluminal stapler for operation according to the present invention includes the cutter for cutting the suturing tissues at the same time as suturing the suturing tissues, two kinds of operating works can be performed, so that it is possible to perform an operation easily and securely.

In addition, since the intraluminal stapler for operation according to the present invention includes a sliding member which is located on the rear surface of the support member and pushes the support member in response to working of the elastic member, it is possible to more easily perform an operation due to its structure.

BRIEF DESCRIPTION OF THE DRAWINGS

The above and other features and advantages of the present invention will become more apparent by describing in detail exemplary embodiments thereof with reference to the attached drawings in which:

FIG. 5 is a perspective view schematically illustrating an intraluminal stapler according to a second embodiment of the present invention;

FIG. 6 is a perspective view schematically illustrating an intraluminal stapler according to a third embodiment of the present invention; and FIG. 7 is a diagram schematically illustrating the working steps of a conventional staple.

BEST MODE FOR CARRYING OUT THE INVENTION

Hereinafter, embodiments of the present invention will be described with reference to FIGS. 1 to 6. The embodiments are intended to exemplify the present invention, but the present invention is not limited to the embodiments.

Figure 1:
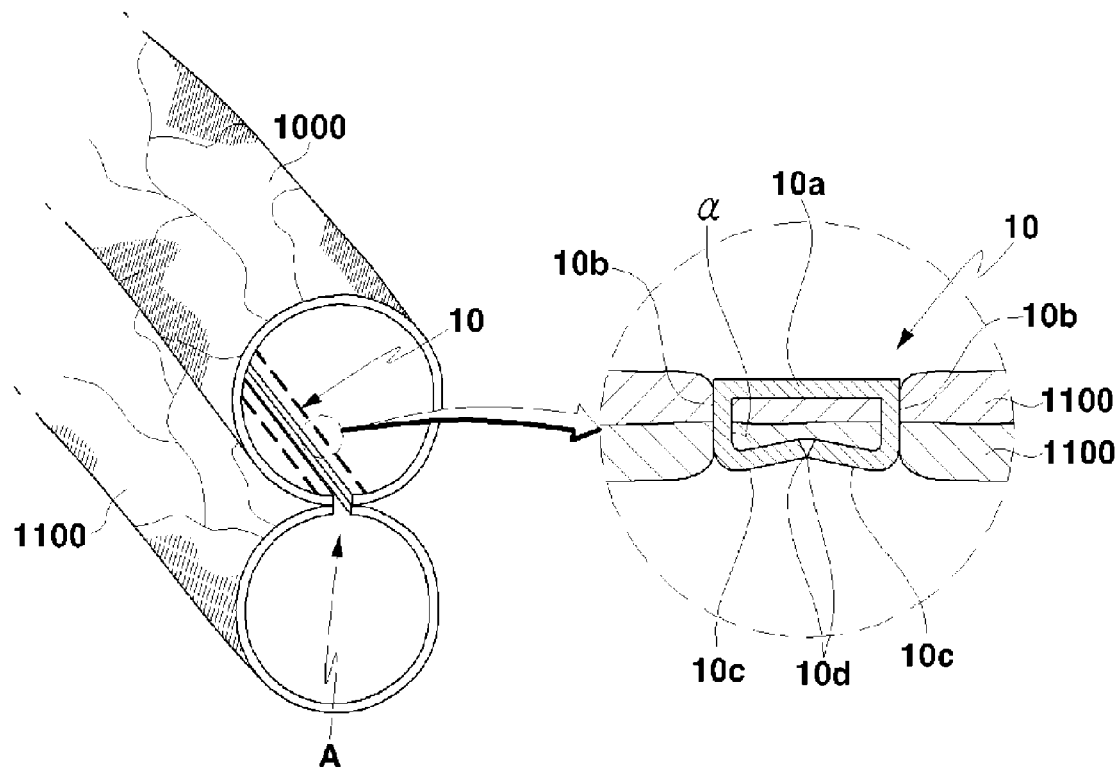
FIG. 1 is a diagram schematically illustrating a state where an operation is performed using staples according to an embodiment of the present invention.

FIG. 1 is a diagram schematically illustrating a state where an operation is performed using a staple according to an embodiment of the present invention, wherein a state where intestines 1000 and 1100 as suturing tissues are anastomosed is schematically shown. Here, the intestines 1000 and 1100 are intended to exemplify suturing tissues to which the present invention would be applied, but the present invention is not limited to it. Therefore, the present invention may be applied to other suturing tissues such as an esophagus, etc.

As shown in FIG. 1, the intestines 1000 and 1100 are anastomosed by staples 10 at Portion A, a portion between a plurality of staples 10 arranged in parallel is cut off by a cutter, thereby closely suturing the intestines 1000 and 1100. The intestine 1000 as a first suturing tissue and the intestine 1100 as a second suturing tissue come in contact with each other and are closely sutured at the time of operation. The staples 10 are attached in parallel to the intestines 1000 and 1100, thereby closely suturing the intestines 1000 and 1100.

A cross-sectional structure of the staple 10 penetrating and closely suturing the intestines 1000 and 1100 is shown in an enlarged circle of FIG. 1. As can be seen from the enlarged circle of FIG. 1, the staple 10 includes a center portion 10a extending on one surface of the intestine 1000, a pair of penetrating portions 10b being bent from both ends of the center portion 10a and penetrating the intestines 1000 and 1100, and a pair of leg portions 10c which is bent from the respective penetrating portions 10b, extends linearly, and closely sutures the intestines 1000 and 1100. The staple 10 may further include another portion as needed. Tensions of the intestines 1000 and 1100 closely sutured are made uniform due to such a structure of the staple 10, so that the suturing operation can be performed securely.

Specifically, since the leg portions 10c of the staple 10 are bent to be opposed to each other, the intestines 1000 and 1100 can be firmly and closely sutured. The leg portions 10c extending from the penetrating portions 10b of the staple are formed not in the rounded shape from the penetrating portions 10b, but in a linear shape to form an angle a with the penetrating portions 10b. Here, since the angle a is an acute angle, the leg portions 10c linearly extend to the surface of the intestine 1100, thereby firmly suturing the intestines 1000 and 1100. In addition, since the angle a is an acute angle, there is almost no possibility that the leg portions 10c penetrate the intestines 1000 and 1100, thereby reducing a risk of bleeding. In addition, since both ends 10d of the leg portions 10c of the staple 10 are in contact with each other, there is almost no possibility that the leg portions 10c re-penetrate the intestines 1000 and 1100. Therefore, it is possible to secure safety of an operation, thereby causing no sequela after an operation.

Figure 2:
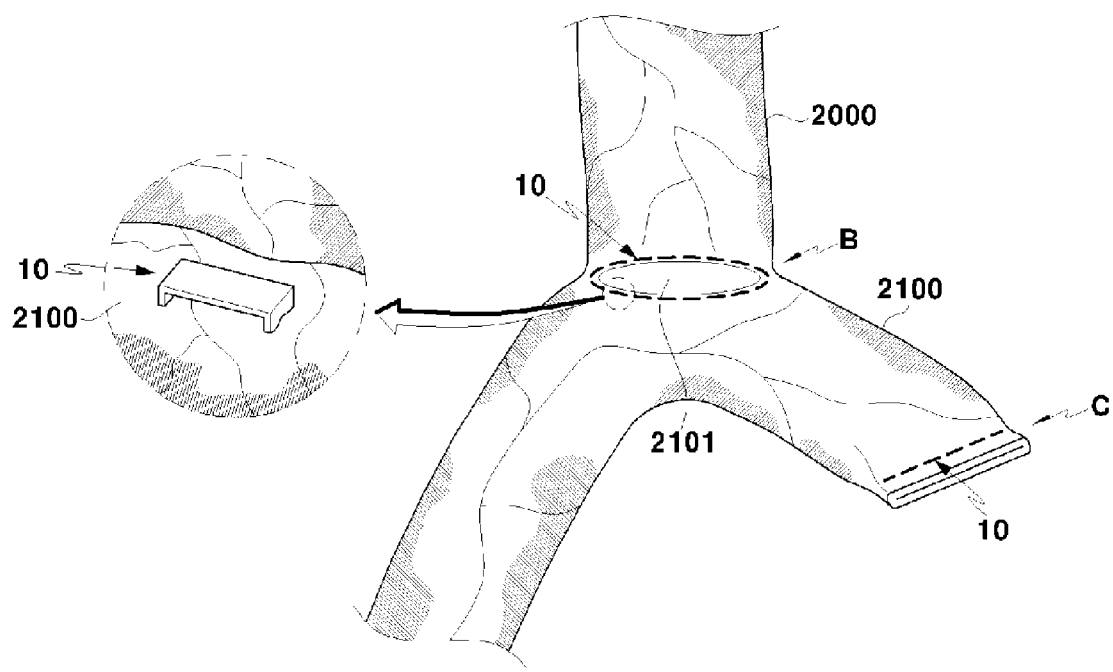
FIG. 2 is a diagram schematically illustrating another state where an operation is performed using the staples according to an embodiment of the present invention.

FIG. 2 is a schematic diagram illustrating another state where an operation is completed using the staples according to an embodiment of the present invention. A state where an esophagus 2000 and an intestine 2100 are anastomosed and sutured after performing a total gastrectomy is shown in the figure. Here, the esophagus 2000 and the intestine 2100 are intended to exemplify the suturing tissues to which the present invention is applied, but the present invention is not limited to the afore-mentioned suturing tissues. Therefore, the present invention may be applied to other suturing tissues.

Portion B and Portion C can be sutured using different intraluminal staplers. In a case of Portion B, before anastomosing the esophagus 2000 and the intestine 2100, the intestine 2100 is bent, an intraluminal stapler is inserted into Portion C not sutured, and the intestine is anastomosed to the inside of the esophagus 2000. Then, the esophagus 2000 and the intestine 2100 are simultaneously sutured and cut off using the intraluminal stapler, thereby forming a hole 2101 for passing foods. The operating staples 10 are attached plurally to the esophagus 2000 and the intestine 2100 in a substantially circular shape, that is, in a circular shape or a shape close to a circle, thereby suturing the esophagus 2000 and the intestine 2100. Next, the intestine 2100 having an opening at Portion C is closely sutured using a different type of intraluminal stapler. Accordingly, the esophagus 2000 and the intestine 2100 can communication with each other, thereby allowing foods to pass well.

In the enlarged circle of FIG. 2, one staple 10 closely suturing the esophagus 2000 and the intestine 2100 is enlarged and shown. As shown in the enlarged circle of FIG. 2, by forming the staple 10 out of a plate, the area of the staple 10 coming in close contact with the esophagus 2000 and the intestine 2100 can be increased, thereby enhance reliability of the close suturing. The staple 10 may be made of titanium having an excellent durability and a corrosion-proof and being not harmful to a human body.

Figure 3:
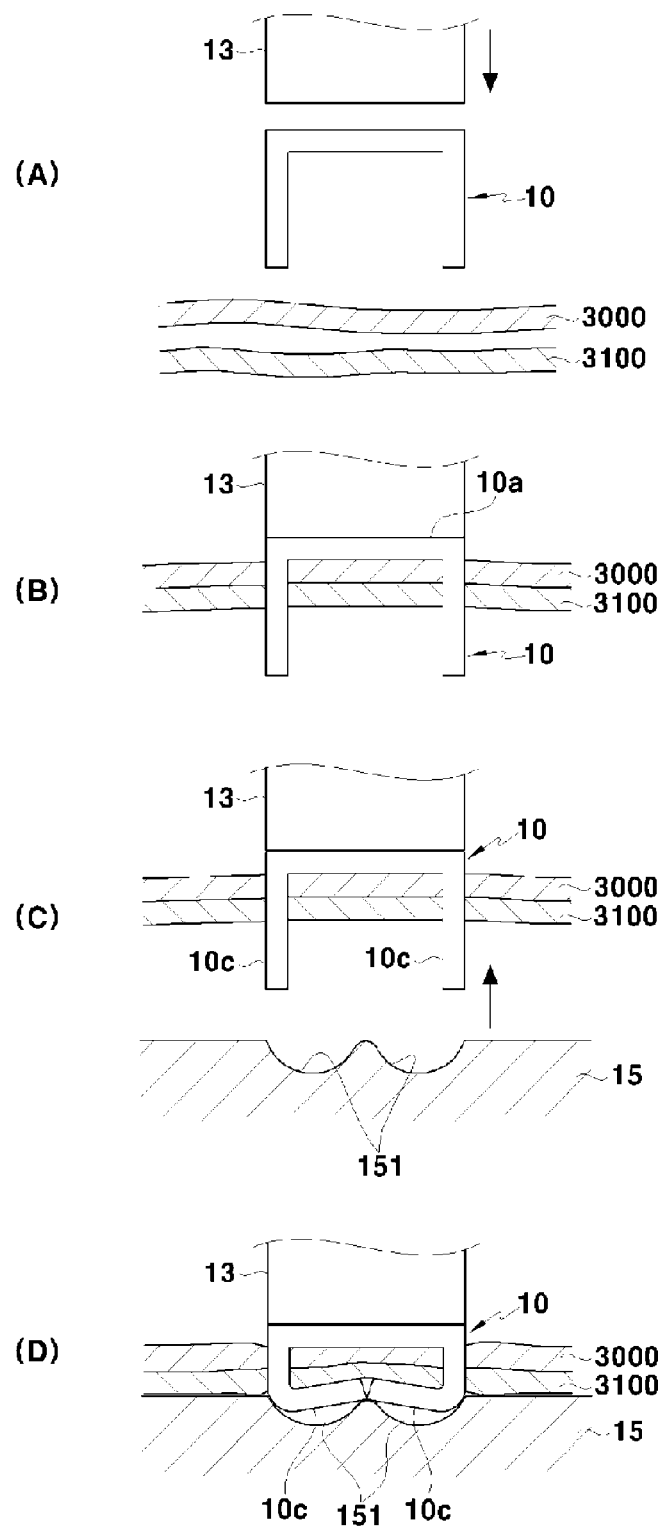
FIG. 3 is a diagram schematically illustrating working steps of a staple according to an embodiment of the present invention.

FIG. 3 is a schematic diagram illustrating working steps of the staple according to an embodiment of the present invention, where a process of suturing the suturing tissues with the staple having the shape shown in FIG. 1 is conceptually illustrated. Now, the steps of suturing the suturing tissues with the staple according to the present invention will be described step by step.

First, as shown in (A) of FIG. 3, the staple 10 is pushed in the arrow direction toward the suturing tissues 3000 and 3100, which are targets to be penetrated, using the push member 13. Accordingly, as shown in (B) of FIG. 3, the staple 10 penetrates the suturing tissues 3000 and 3100, and the center portion 10a thereof are closely fixed to the upper surface of the suturing tissue 3000. Since the push member 13 continuously presses the center portion 10a of the staple 10, the center portion 10a is closely in contact with the upper surface of the suturing tissue 3000.

Next, as shown in (C) of FIG. 3, a support member 15 is made to approach the leg portions 10c of the staple 10. Since grooves 151 are formed in the support member 15, the support member 15 comes in contact with the leg portions 10c of the staple 10 and then bends the leg portions 10c. In this way, as shown in (D) of FIG. 3, the leg portions 10c is first subjected to a force toward the inside and a supporting force by the tissues at the portions penetrating the tissues, so that these portions are first bent. As a result, the leg portions 10c are linearly bent and are closely fixed to the lower surface of the suturing tissue 3100. In this way, since the suturing tissues 3000 and 3100 can be firmly and closely sutured, it is possible to secure safety of an operation, so that the risk of bleeding from the sutured portions can be reduced.

As shown in FIG. 3, in the present invention, since the step of penetrating the suturing tissues 3000 and 3100 using the push member 13 and the step of bending the leg portions 10c of the staple 10 using the support member 15 are performed not simultaneously, but sequentially, the leg portions 10c can be linearly bent. As a result, the tensions of the suturing tissues 3000 and 3100 can be made uniform, thereby keeping the sutured state firm. In this way, the operation of closely suturing the suturing tissues 3000 and 3100 sequentially using the operating staples 10 can be performed using the intraluminal stapler having the operating staples 10. Now, the intraluminal stapler for operation having the operating staples 10 suturing the suturing tissues as shown in FIG. 3 will be described in detail with reference to FIGS. 4 to 6.

Figure 4:
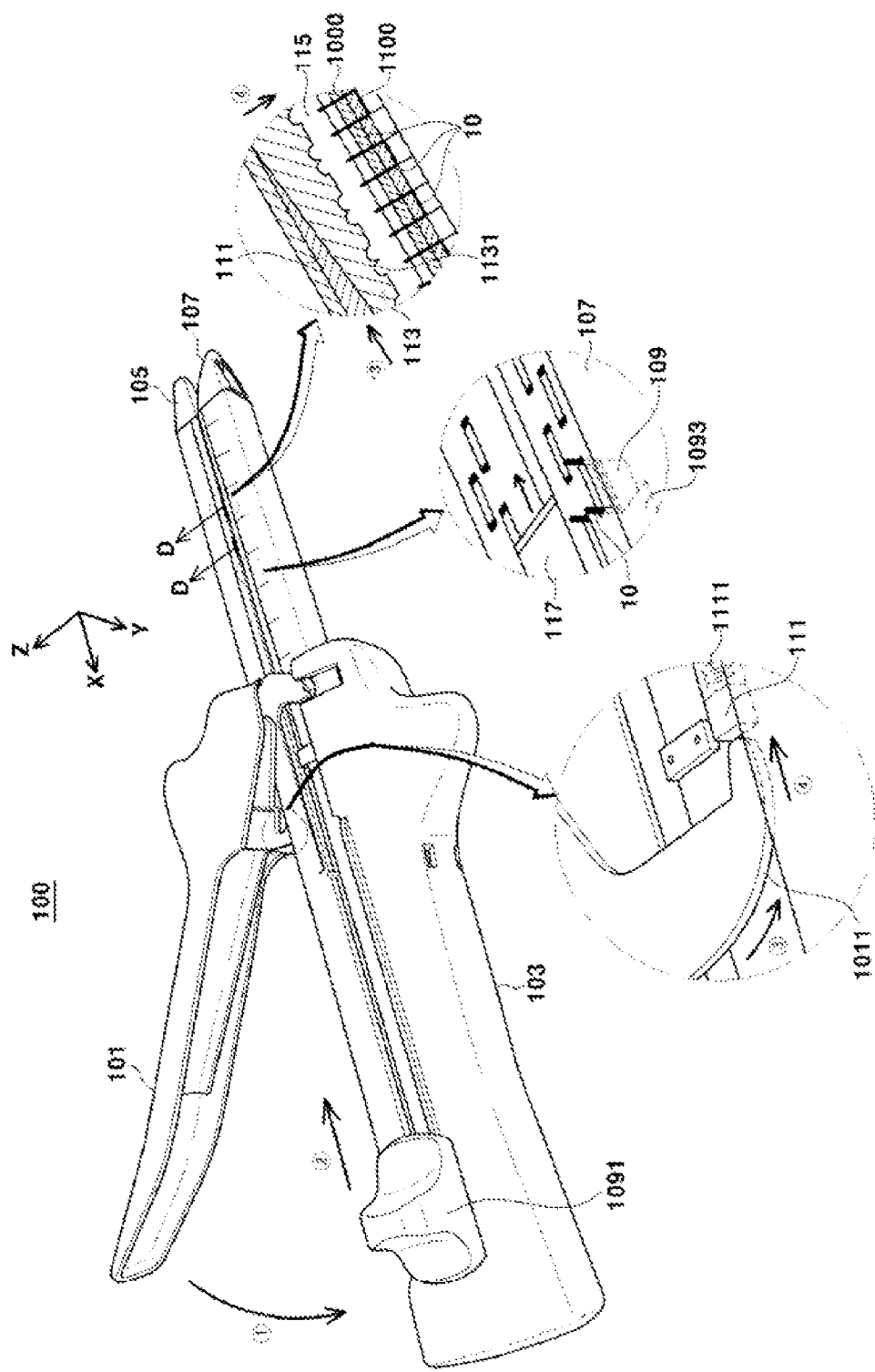
FIG. 4 is a perspective view schematically illustrating an intraluminal stapler according to a first embodiment of the present invention.

FIG. 4 is a perspective view schematically illustrating an intraluminal stapler 100 according to a first embodiment of the present invention, in which a linear stapler (GIA) for cutting and suturing a tissue is illustrated. The intraluminal stapler 100 shown in FIG. 4 is used for closely suturing Portion A of FIG. 1. An internal structure of a main body 103 is schematically shown in the left enlarged circle of FIG. 4, a lower inserting rod 107 as seen in the Z axis direction is shown in the central enlarged circle, and a cross-section of an upper inserting rod 105 taken along Line D-D is shown in the right enlarged circle. The intraluminal stapler 100 according to the first embodiment of the present invention shown in FIG. 4 is intended to exemplify the present invention, but the present invention is not limited to the above stapler. Therefore, the present invention may be applied to another type of intraluminal stapler.

In FIG. 4, the inserting rods 105 and 107 of the intraluminal stapler 100 are opened and inserted into the intestines 1000 and 1100, respectively, and then the intestines 1000 and 1100 are cut off and then closely sutured using a push member button 1091 and a trigger 101 provided in a main body 103.

The intraluminal stapler 100 for operation according to the first embodiment of the present invention shown in FIG. 4 includes the operating staples 10, the trigger 101, an elastic member 111, a support member 113, and a housing 115. The respective components are organically coupled to the main body 103 and other members may be further provided as needed.

The trigger 101 is mounted at one side of the intraluminal stapler 100 for operation and can work with a hand. The elastic member 111 longitudinally extends through the inside of the main body 103 of the intraluminal stapler 100, and includes a spring 1111 therein. When the trigger 101 works, the elastic member 111 comes in contact with an manipulating portion 1011 of the trigger 101. As shown in the right enlarged circle of FIG. 4, the rear surface of the support member 113 is connected to the elastic member 111, and the support member 113 works by the elastic member 111. Grooves 1131 are formed in the support member 113 and bend both ends of the staples 10.

As shown in the right enlarged circle of FIG. 4, an inner space for receiving the support member 113 is formed in the housing 115. The ends of the staples 10 penetrating the suturing tissues 1000 and 1100 in response to the manipulation of the trigger 101 are positioned in the inner space of the housing 115. The support member 113 positioned in the inner space of the housing 115 is moved out of the inner space with the working of the elastic member 111. Here, the support member 113 is guided to the ends of the staples 10 and bends the staples 10.

Since the remaining structure of the intraluminal stapler 100 according to the first embodiment of the present invention shown in FIG. 4 can be easily understood by those skilled in the art, description thereof will be omitted. Now, a process of closely suturing the intestines 1000 and 1100 using the intraluminal stapler 100 shown in FIG. 4 will be sequentially described in detail.

First, in the step of ①, the inserting rods 105 and 107 are inserted into the upper and lower suturing tissues 1000 and 1100, and the trigger 101 is pressed in the arrow direction with a hand. As a result, the opened inserting rods 105 and 107 come close to each other. Next, as shown in the left enlarged circle of FIG. 4, when the elastic force of the elastic member 111 is felt by the hand as soon as the manipulating portion 1011 of the trigger 101 comes in contact with the elastic member 111, the working of the trigger 101 is stopped. The trigger 101 may be fixed not to move as needed.

Next, in the step of ②, the push member button 1091 guided to the main body 103 is pushed in the X axis direction.

Accordingly, as shown in the central enlarged circle of FIG. 4, a connection member 1093 connected to the push member button 1091 moves a cutter 117 in the arrow direction and thus pushes the push member 109. The cutter 117 is spaced in parallel from the plurality of staples 10 and cuts off the suturing tissues 1000 and 1100 in contact with each other by means of movement of the push member 109. The push member 109 pushes the staples 10 such that the staples 10 penetrate the suturing tissues 1000 and 1100 until the trigger 101 comes in contact with the elastic member 111. Since the connection member 1093 and the push member 109 have a slope surface contacting each other, the push member 109 pushes out the staples 10 fixed to the upside while moving upwardly. As a result, as shown in the right enlarged circle of FIG. 4, the staples 10 penetrate the suturing tissues 1000 and 1100, so that the ends thereof are suspended in the inner space.

In the step of ③, the paused trigger 101 is made to work again and pushes the elastic member 111 extending along the main body 103. Accordingly, as shown in the right enlarged circle of FIG. 4, in the step of ④, the support member 113 is pushed toward the staples 10 by means of movement of the elastic member 111 of which one end is sloped. As a result, the ends of the staples 10 can be bent, thereby closely suturing the suturing tissues 1000 and 1100.

Since the suturing tissues 1000 and 1100 can be closely sutured by the staples 10 having the structure shown in FIG. 1 using the intraluminal stapler 100 having the aforementioned structure, the bleeding from the sutured portion can be decreased, as well as the safety during an operation can be enhanced.

FIG. 5 is a perspective view schematically illustrating an intraluminal stapler 200 according to a second embodiment of the present invention, in which a circular stapler (EEA) is shown. The intraluminal stapler 200 shown in FIG. 5 is used for closely suturing Portion B of FIG. 2. A cross-section of an anvil 221 taken along Line E-E is shown in the left enlarged circle of FIG. 5, and an internal structure of a main body 203 is schematically shown in the right enlarged circle of FIG. 5. The intraluminal stapler 200 according to the second embodiment of the present invention shown in FIG. 5 is intended to exemplify the present invention, but the present invention is not limited to the aforementioned stapler. Therefore, the present invention may be applied to another type of intraluminal stapler.

The intraluminal stapler 200 shown in FIG. 5 approximately includes the anvil 221 and the main body 203, and a cutter (not shown) and staples (not shown) are received in the upper end of the main body 203. The cutter and the staples are moved upwardly with rotation of a handle 2091 and are protruded from the main body 203 with the pressing of the trigger 201, so that the suturing tissues can be cut off and sutured using the cutter (not shown) and the staples (not shown).

The other structure of the intraluminal stapler 200 according to the second embodiment of the present invention can be easily understood by those skilled in the art, detailed description thereof will be omitted. Now, a process of closely suturing an esophagus 2000 and an intestine 2100 shown in FIG. 2 using the intraluminal stapler 200 shown in FIG. 5 will be sequentially described in detail.

First, in the step of ①, the anvil 221 is separated from the main body 203 and is inserted into the esophagus 2000 shown in FIG. 2. The end of the anvil is fixed with a thread and a shaft 223 is extracted from the lower portion. The main body 203 is inserted into Portion C of the intestine 2100 shown in FIG. 2 and pierces the side surface of the intestine 2100. Then, the main body 203 is coupled to the shaft 223, and the main body 203 comes close to the lower portion of the anvil 221 with rotation of the handle 2091. Accordingly, the main body 203 comes close to the housing 215 shown in the left enlarged circle of FIG. 5.

Next, in the step of ②, as shown in the right enlarged circle of FIG. 5, when the trigger 201 is pressed, the manipulating portion 2011 of the trigger pushes the push member 209. Since the push member 209 is connected to the cutter and the staples positioned at the upper end of the main body 203 through the inside of the main body 203, the cutter and the staples are pushed and protruded toward the outside of the main body 203, thereby cutting off and positioning the suturing tissues in the inner space of the housing 215. Subsequently, when the manipulating portion 2011 of the trigger comes in contact with the elastic member 211, an elastic force is delivered to the hand due to a spring 2111 included in the elastic member 211, and at that time, the working of the trigger 201 is stopped.

In the step of ③, the stopped trigger 201 is subsequently pressed to push the elastic member 211. As shown in the left enlarged circle of FIG. 5, the elastic member 211 pushes a sliding member 219 received in the anvil 221. Since the sliding member 219 is positioned in a sealed space, the sliding member slides in the opposite direction of a direction in which the elastic member 211 pushes the sliding member and is smoothly moved.

In the step of ④, since the sliding member 219 is positioned on the rear surface of the support member 213, the support member 213 can be pushed by means of movement of the elastic member 211. Accordingly, the ends of the staples 10 can be bent with the grooves 2131 formed in the lower portion of the support member 213.

In this way, by firmly and closely suturing the esophagus and the intestine while forming an opening portion in the esophagus and the intestine, foods can be made to pass through the opening portion.

FIG. 6 is a perspective view schematically illustrating an intraluminal stapler according to a third embodiment of the present invention, in which a linear stapler (TA) performing only the suturing is shown. The intraluminal stapler 300 shown in FIG. 6 is used for closely suturing Portion C of FIG. 2. An internal structure of a main body 303 is schematically shown in the left enlarged circle of FIG. 6, and a cross-section of a head section 305 taken along Line F-F is shown in the right enlarged circle of FIG. 6. The intraluminal stapler 300 according to the third embodiment of the present invention shown in FIG. 6 is intended to exemplify the present invention, but the present invention is not limited to the aforementioned intraluminal stapler. Therefore, the present invention may be applied to another type of intraluminal stapler.

The intraluminal stapler 300 according to the third embodiment of the present invention shown in FIG. 6 approximately includes the main body 303 and the head section 305, and closely suturing the suturing tissues with the staples 10 by pressing a trigger 301. Since constituent components of the intraluminal stapler 300 according to the third embodiment of the present invention are similar to the constituent components of the intraluminal stapler according to the first and second embodiments of the present invention, detailed description thereof will be omitted. Since the other structure of the intraluminal stapler 300 according to the third embodiment of the present invention shown in FIG. 6 can be easily understood by those skilled in the art, detailed description thereof will be omitted. Now, a process of closely suturing the suturing tissues using the intraluminal stapler 300 shown in FIG. 6 will be sequentially described in detail.

In the step of ①, the trigger 301 is pulled in the arrow direction and the manipulating portion 3011 of the trigger works to push the push member 309. Accordingly, the head section 3051 is moved upwardly and comes close to an upper section 3052 of the head section, thereby biting and fixing the suturing tissues therebetween. Subsequently, manipulating portion of the trigger 3011 comes in contact with the elastic member 311 having a spring 3111, and when the elastic force is felt, the trigger 301 is stopped.

Next, in the step of ②, as shown in the right enlarged circle of FIG. 6, by pushing the push member button 3091, the push member 309 connected to the push member button 3091 protrudes the staples 10 from the head section 3051. At this time, the staples 10 penetrate the suturing tissues and are received in the inner space of the housing 315.

In the step of ③, subsequently, the trigger 301 is pulled and then the elastic member 311 is pushed. Accordingly, as shown in the right enlarged circle of FIG. 6, in the step of ④, the support member 313 having grooves 3131 is protruded downwardly by pushing the sliding member 319 with the elastic member 311, thereby bending the ends of the staples 10 and closely suturing the suturing tissues.

Although not shown in the figure, the operating staples according to the present invention can be also used for laparoscopy. The GIA type intraluminal stapler can be used for laparoscopy. However, since the intraluminal stapler has a restriction that the stapling portion has to enter a diameter of 12 mm for the laparoscopy, the operating staples according to the present invention can be utilized, by reducing the length of the leg portions of the staples and thus allowing more staples to enter a constant length.

Although the present invention has been described in conjunction with the embodiments, it should be understood by those skilled in the art that various modifications and changes can be made thereto without departing from the gist and scope of the appended claims.

The invention claimed is:

1. A method for operating an intraluminal stapler having an operating staple, the method comprising:
   pressing a trigger until a manipulating portion of the trigger contacts an elastic member;
   after the manipulating portion of the trigger has contacted the elastic member, pushing a push member button such that a connection member connected to the push member button moves a cutter spaced in parallel from the operating staple, and thus pushes the operating staple through a plurality of suturing tissues such that an end of the operating staple protrudes from the plurality of suturing tissues; and
   after the operating staple has been pushed through the plurality of suturing tissues, linearly pushing the elastic member by working the trigger again, thereby pushing a support member toward the end of the operating staple and bending the operating staple, thereby closely suturing the plurality of suturing tissues, wherein the support member contacts the end of the operating staple before it contacts either of the plurality of suturing tissues.

2. A method of stapling a plurality of tissues together, the method comprising:
   providing an intraluminal stapler that includes a cutter, a staple, a push member and a support member, wherein the push member and support member are positioned adjacent to each other and are movable with respect to each other;
   pushing the staple with the push member, such that a leg portion of the staple penetrates the plurality of tissues, wherein (a) a proximal region of the leg portion of the staple passes through the plurality of tissues, (b) a distal region of the leg portion of the staple protrudes from the plurality of tissues, and (c) a center portion of the staple contacts one of the plurality of tissues;

once the center portion of the staple contacts one of the plurality of tissues, pressing an end of the leg portion of the staple into a groove formed in the support member, such that an acute angle is formed in the leg portion of the staple wherein (a) the proximal region of the leg portion remains substantially linear between the center portion of the staple and the acute angle, and (b) the distal region of the leg portion does not pass through the tissues and also remains substantially linear; and using the cutter to cut the plurality of tissues while pushing the staple with the push member.

\* \* \* \* \*